(12) United States Patent
Cabrera et al.

(10) Patent No.: US 11,340,189 B2
(45) Date of Patent: May 24, 2022

(54) ELECTROCHEMICAL IMPEDIMETRIC BIOSENSING MICROCHIP FOR REAL TIME TELOMERASE ACTIVITY DETECTION

(71) Applicants: Carlos Raul Cabrera, San Juan, PR (US); Lisandro Federico Cunei, San Juan, PR (US); Carlos I. Gonzalez, Trujillo Alto, PR (US); Marina Martinez-Vargas, Naguabo, PR (US)

(72) Inventors: Carlos Raul Cabrera, San Juan, PR (US); Lisandro Federico Cunei, San Juan, PR (US); Carlos I. Gonzalez, Trujillo Alto, PR (US); Marina Martinez-Vargas, Naguabo, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 14/954,376

(22) Filed: Nov. 30, 2015

(65) Prior Publication Data

US 2018/0252663 A1 Sep. 6, 2018

Related U.S. Application Data

(60) Provisional application No. 62/089,290, filed on Dec. 9, 2014.

(51) Int. Cl.
*G01N 27/327* (2006.01)
*G01N 33/573* (2006.01)
*C12Q 1/6825* (2018.01)

(52) U.S. Cl.
CPC .. *G01N 27/3275* (2013.01); *C12Y 207/07049* (2013.01); *G01N 33/573* (2013.01); *C12Q 1/6825* (2013.01); *G01N 2333/912* (2013.01)

(58) Field of Classification Search
CPC ............ G01N 27/3275; G01N 33/573; G01N 33/574; C12Y 207/07049; C12Q 1/6816; C12Q 1/6825
See application file for complete search history.

(56) References Cited

U.S. PATENT DOCUMENTS

| | | | |
|---|---|---|---|
| 7,208,077 B1 * | 4/2007 | Albers | G01N 27/3277 204/403.01 |
| 2005/0244886 A1 * | 11/2005 | Iwadate | C12Q 1/6874 435/6.11 |

(Continued)

OTHER PUBLICATIONS

Cunei et al. (RSC Adv, 4, 52357) (Year: 2014).*

(Continued)

*Primary Examiner* — Alexander S Noguerola
(74) *Attorney, Agent, or Firm* — Hoglund & Pamias, PSC; Roberto J Rios

(57) ABSTRACT

The enzyme telomerase is present at about 85% of human cancers that makes it not only an excellent target for cancer treatment but also an excellent marker for cancer detection. Using a single stranded DNA probe specific for telomerase binding and reverse transcription tethered to an interdigital gold electrode array surface, the chromosome protection provided by the telomerase was replicated and followed by Electrochemical Impedance Spectroscopy as an unlabeled biosensor. Using a custom system, which is simple and affordable, the impedance measurements were taken while incubating at 37° C. and promoting the probe elongation. This resulted in up to 14-fold increase in the charge transfer resistance when testing a telomerase-positive nuclear extract from Jurkat cells compared to the heat-inactivated telomerase-negative nuclear extract. The electron transfer process at the Au electrodes was studied before and after the (Continued)

elongation, after 4 months in contact with the telomerase-positive nuclear extract, and after desorption of the non-specific bindings.

11 Claims, 8 Drawing Sheets

Specification includes a Sequence Listing.

(56) References Cited

U.S. PATENT DOCUMENTS

| | | | |
|---|---|---|---|
| 2011/0317739 A1* | 12/2011 | Cole | G01K 7/028 374/179 |
| 2012/0058472 A1* | 3/2012 | Hsing | C12Q 1/6825 435/6.11 |
| 2013/0315782 A1* | 11/2013 | Huang | G01N 27/00 422/69 |

OTHER PUBLICATIONS

Wu et al. (Adv. Funct. Mater. 24, 2727) (Year: 2014).*
Chapman et al. (Langmuir 16, 6927) (Year: 2000).*
AllFlex (accessed Aug. 16, 2018) (Year: 2013).*
RTD (author unknown) (Year: 2003).*
Krommenhoek et al. (Anal. Chem. 79, 5567-5573 (Year: 2007).*

* cited by examiner

SEQUENCE LISTING

```
<160> NUMBER OF SEQ ID NOS: 1

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 ttttttttt aatccgtcga gcagagtt                                           28
```

ELECTROCHEMICAL IMPEDIMETRIC BIOSENSING MICROCHIP FOR REAL TIME TELOMERASE ACTIVITY DETECTION

FEDERAL GRANTS

This research was supported, in part by the National Science Foundation (NSF) through their CHE-1152940 grant. The Government has certain rights in this invention.

SEQUENCE LISTING

The instant application contains a Sequence Listing which has been filed electronically in ASCII format and is hereby incorporated by reference in its entirety. Said ASCII copy, created on January 2018, is named UPR-14231_Sequence_Listing_Final and is 690 bytes in size.

BACKGROUND OF THE INVENTION

Human chromosomes have at their very end DNA sequences known as telomeres, which are shortened in every cell replication cycle. These telomeres consist of tandem repeats of species-dependent G-rich sequence (particularly in vertebrates, 5'-TTAGGG-3'). Due to the continuous shortening of these DNA sequences during cell replication, "healthy" somatic cells cannot go beyond the Hayflick limit of cell division. However, the majority of cancer cells (approximately 85%) have found a loophole, activating the Telomerase enzyme. Cancer cells that do not activate telomerase, use an alternative mechanism known as alternative lengthening of telomeres (ALT), which is still not completely understood. The vast presence and activity of the enzyme telomerase in cancer cells makes it a suitable target for diagnosis and treatment. Also, inhibition of Telomerase activity is known to induce tumor cell growth arrest. In immortal cells, such as the Jurkat T cell line used in this invention, Telomerase aids in the maintenance of telomeres.

Several biosensors for the detection of telomerase as a cancer marker have been reported within the last few years. The most promising biosensor platforms that specifically detect telomerase rely on the principle of the elongation of single stranded DNA probes with specific sequences, such as 5'-TTAGGG-3' for vertebrates. Using this principle, many electrochemical telomerase biosensors have been reported using differential pulse voltammetry, electroluminescence, and chronocoulometry, with only one that uses electrochemical impedance spectroscopy (EIS) for a dual purpose: for surface characterization and as the biosensor signal transducer.

There are numerous advantages of using EIS in biosensor design, such as high sensitivity accuracy, rapid detection, compatibility with microfabrication technology and real-time measurements. In the detection of telomerase, EIS has been used in one instance where a ssDNA oligomer probe was tethered to the surface of a gold disk electrode, and incubate the electrode in a HeLa cell extract for several hours. Then, the electron transfer reaction of the ferricyanide/ferrocyanide redox couple was measured in a different buffer by EIS, and correlated the electron transfer resistance to the elongation of the probe. However, these reported biosensor configurations only considered the ferricyanide/ferrocianyde redox reaction and none have taken advantage of the vast diversity of molecules already in total/nuclear cell extracts and buffer solutions.

SUMMARY OF THE INVENTION

The present invention provides hardware system and associated simple and user-friendly software for an in-situ incubation while the presence of the enzyme telomerase as a cancer marker is detected by taking advantage of its reverse transcriptase activity measured in real time. For experimental purposes, Jurkat T cells, which have been useful in studies of Telomerase activity regulation and in understanding the mechanisms of differential susceptibility of several cancers to radiation and other treatments, were used. A nuclear extract of Jurkat cells in the absence of an additional redox couple was used as the telomerase-positive sample, and a solution heat treated at 95° C. to inactivate the telomerase enzyme as the control. This invention provides straightforward detection of telomeric activity in under 20 minutes using a robust, powerful and scalable method, using an interdigital biosensor microchip and avoiding the need of a reference electrode. Accordingly, this invention is a step toward cheaper and faster cancer detection at the point of care.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Experimental
Software and Hardware for Temperature Control

The software was made using all open source components, which are available in the internet free of cost. The programming language for the desktop client is JAVA® Version 7, from ORACLE® free of charge. We developed a proprietary serial protocol for communication with the circuit and the main algorithm for controlling the same. The rest of the functionality was created using pre-existing libraries. The graphics are plotted using JFREECHART and the low-level serial communication is done using Neuron-Robotics's nrjavaserial library.

Figure 7:
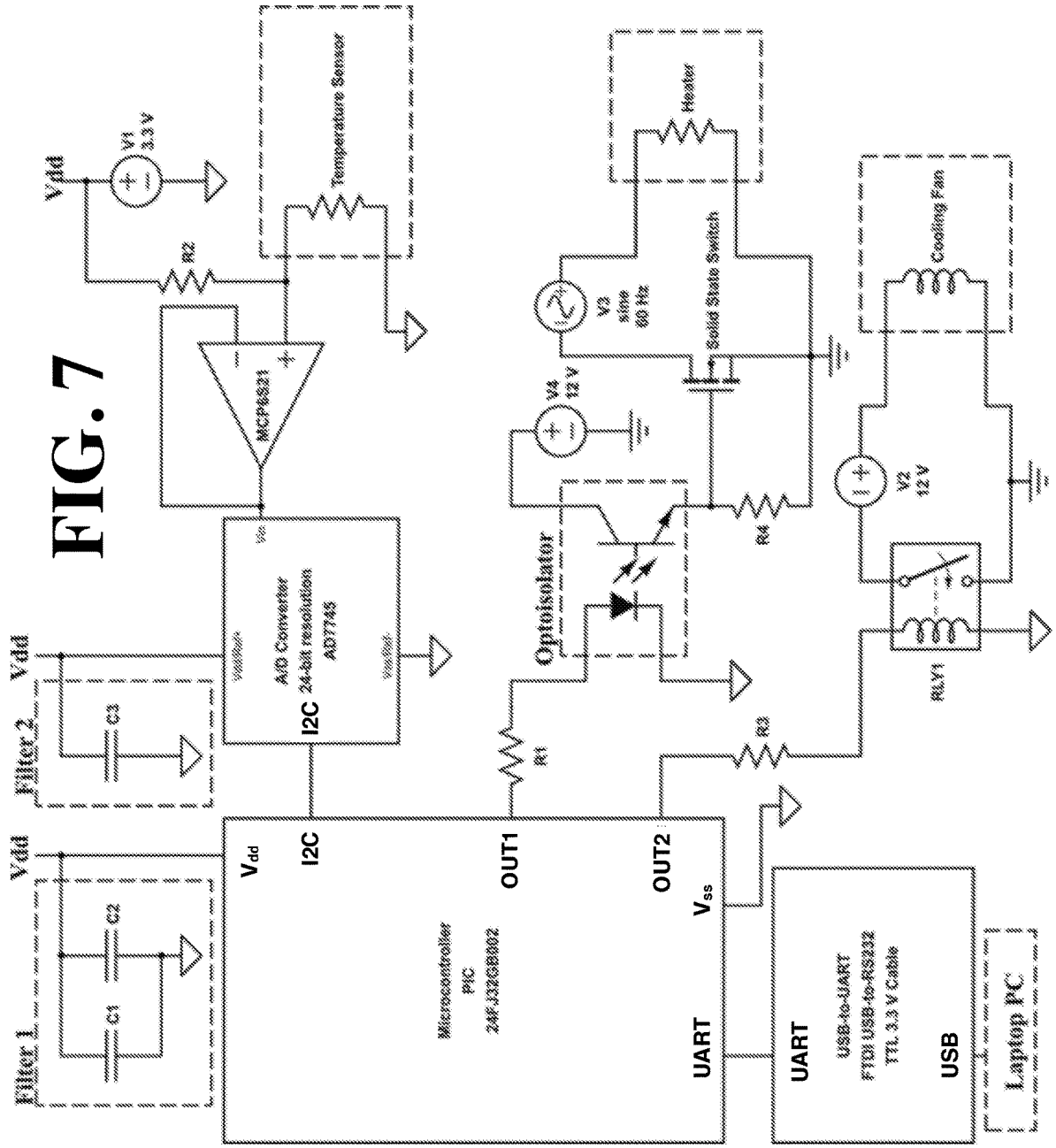
FIG. 7 shows the electronic circuit scheme for the temperature controller.
Figure 8:
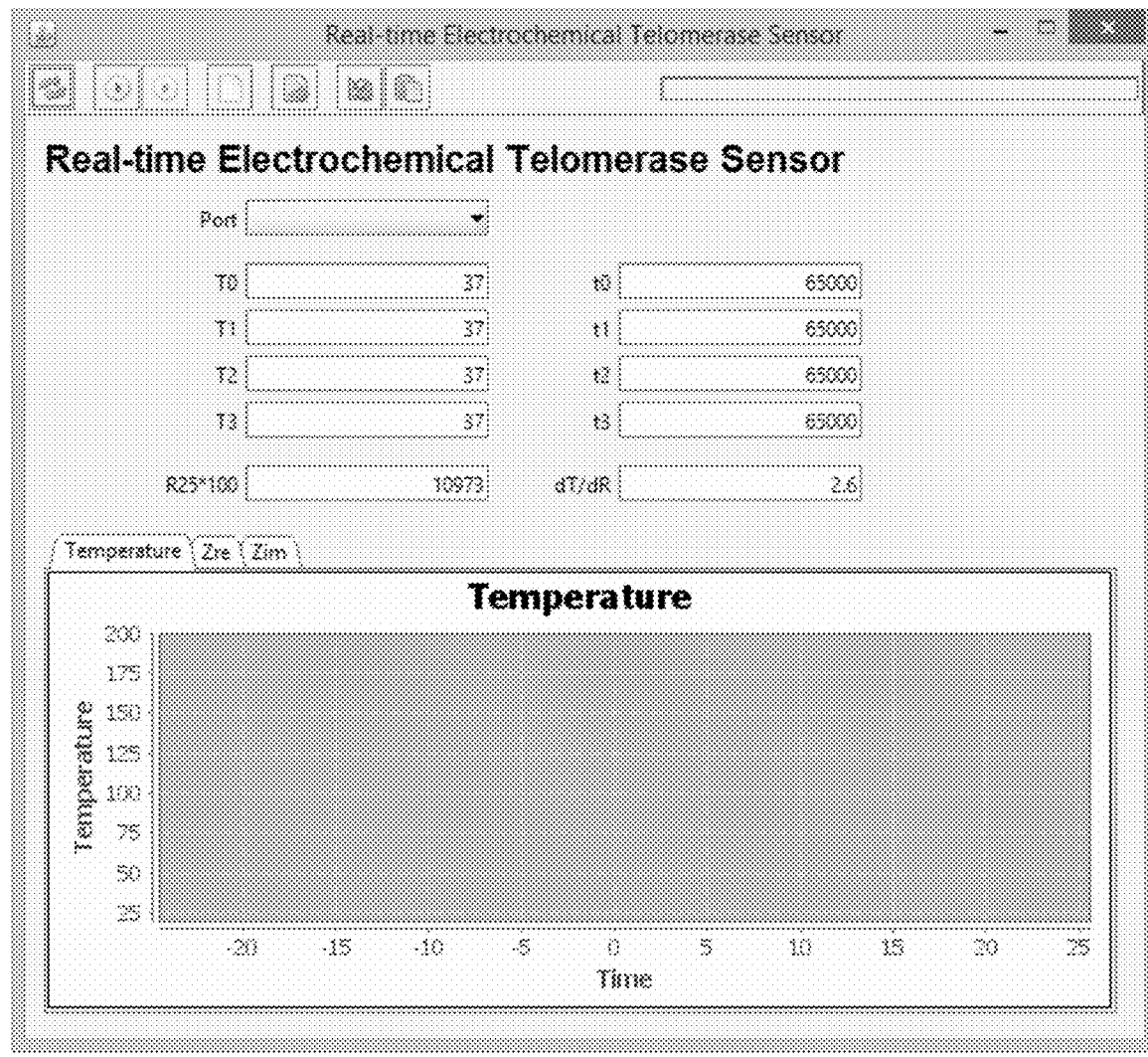
FIG. 8 illustrates a screen of the software designed to control the temperature for the incubation.

The hardware of the present invention is inexpensive and easy to implement. The temperature controller was built with commercially available components in order to allow construction with off-the-shelf components. A scheme of the circuit is illustrated in FIG. 7. The circuit was soldered manually, and an explanation of how it works is provided below. We used a potentiostat for accurate EIS measurements but simple impedance measurement circuits can be modified to work with this system while reporting to the same software.

Microchip Fabrication

The biosensor interdigital gold electrode array microchip was fabricated by using 500 µm thick, 100 mm dia., single side polished, <100> oriented silicon wafers where we deposited ca. 200 nm of $SiO_2$ by Plasma-Enhanced Chemical Vapor Deposition as isolation. Then, we used S1813 (Shipley) photoresist which was spinned at 3000 rpm for 60 seconds before pre-baking for 60 seconds at 115° C. A Suss Microtec MA6 Mask Aligner with a 400 nm, 350 W, UV lamp was used with our photolithography mask (Front Range Photomask). Then, we deposited 5 nm of Ti and 150 nm of Au in a CHA SE-600 electron beam evaporator, after which we proceeded with the photoresist lift-off in acetone.

Positive and Control Nuclear Extracts Preparation

Cell Culture

Jurkat T Cells (from the American Type Culture Collection of Manassas, Va., USA) were incubated at 37° C. with 5% $CO_2$ using RPMI-1640 media (Hyclone) complemented with 10% Fetal Bovine Serum (Hyclone) and an antibiotic/antimycotic that consisted of penicillin, streptomycin and amphotericin B (Sigma).

Nuclear Cell Extract

Jurkat T cells ($1 \times 10^6$ cell/ml) were harvested. The cells were washed twice with cold 1×PBS (140 mM NaCl, 2.7 mM KCl, 10 mM $NaHPO_4$, and 1.8 mM $KH_2PO_4$) and centrifuged at 1,500 rpm for 5 min. The supernatant was discarded and the pellet was resuspended in buffer A (10 mM HEPES-KOH [pH 7.9], 1.5 mM $MgCl_2$, 10 mM KCl, 1 mM DTT and 1 mM PMSF). The mixture was incubated on ice for 10 min and centrifuged at 1,500 rpm for 10 min at 4° C. The supernatant was discarded; fresh buffer A was added to the pellet and lysed in a 7 ml Dounce homogenizer (Kontes). The lysate was centrifuged at 6,500 rpm for 2 min at 4° C. in order to separate the nuclei (pellet) from the cytoplasm (supernatant). The nuclei fraction was resuspended in 1 ml of the Buffer C (20 mM HEPES [pH 7.9], 0.42 M NaCl, 0.2 mM EDTA, 25% Glycerol, 1.5 mM $MgCl_2$, 0.5 mM PMSF and 0.5 mM DTT) and a handy-sonifier was used to disrupt the fraction by sonicating 6 times for 10 sec at maximum power. Nuclei fraction was centrifuged at maximum rpm for 30 min at 4° C. Then, the nuclear extract was stored at −80° C.

Control Solution

The control solution was prepared by a procedure previously reported in the literature, we heated the Jurkat cell nuclear extract to 95° C. for 10 minutes, which readily inactivates telomerase activity.

DNA Self-Assembled Monolayer Deposition

Figure 2:
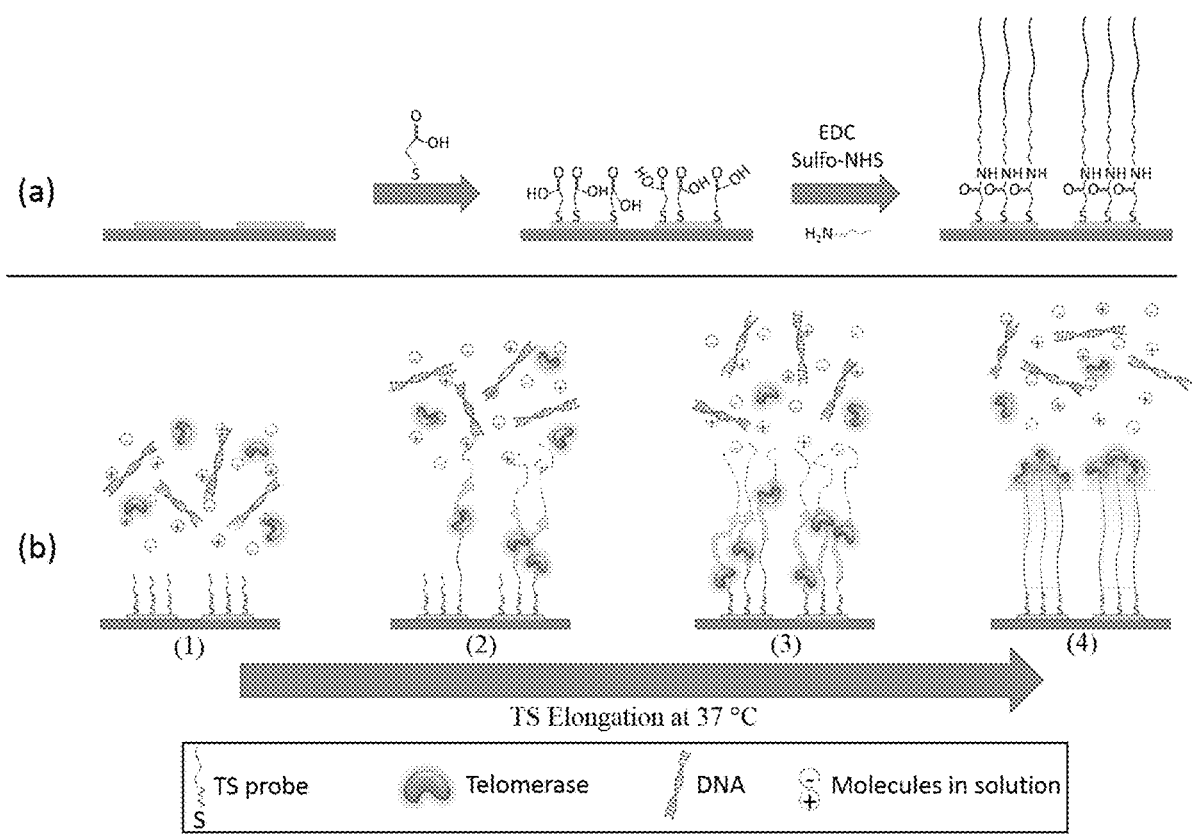
FIG. 2 illustrates the procedure for the tethering of the TS probes and the mechanism responsible for the expected change in the impedance during incubation at 37° C.

The immobilization of the ssDNA probe was carried out as follows. After cleaning in piranha solution for 30 minutes, the interdigital electrode arrays (IDA) were exposed to an aqueous solution of 2 mM Thioglycolic Acid overnight, which formed a SAM that left an exposed carboxyl group. This group was reacted with a solution of EDC 20 mM and Sulfo-NHS mM for 2 hours after which a solution of 1 µM $NH_2$—$(CH_2)_6$-TS (5'-$NH_2(CH_2)_6$TTTTTTTTT-TAATCCGTCGAGCAGAGTT-3') (SEQ ID NO:1) was deposited on the modified IDA and left overnight. Then, the IDA were washed carefully and treated with nanopure water, then, dried with $N_2$. After that, we carefully washed with 40 mM $NH_2OH.HCl$ and 0.05% SDS, and finally dried with $N_2$ again to be used the same day. The O-ring rubbers were maintained in ethanol until needed for the electrochemical cell ensemble, when they were washed with nanopure water, dried with $N_2$ and placed on the IDA. Finally, 20 µl of nuclear extract solution was added inside the O-ring and closed with a piece of clean glass slide. FIG. 2a shows a schematic of the procedure used for the tethering of TS to the interdigital gold surface electrodes.

Electrochemical Measurements

The electrochemical experiments were done in an Autolab PGSTAT30 potentiostat. EIS experiments were conducted from 1.0 MHz to 0.1 Hz taking 40 measurements in logarithmic scale, with an amplitude of 10 $mV_{p-p}$, single sine method, at 0.00 V applied voltage between the two electrodes. The open circuit voltages were taken just before the experiments from the potentiostat front panel, and they all measured equal or less than 0.01 V that was used to verify that both electrodes were similar before starting.

DNA Visualization

A solution of 10×TAE buffer (pH 8.18-8.29) was prepared by mixing 48.4 g of Tris-base (Sigma-Aldrich), 10.9 g of Glacial Acetic Acid (Sigma-Aldrich), and 2.92 g of EDTA (Sigma-Aldrich) in 1 L of nanopure water. The dilution of 1 g of agarose (BioRad) was done in 100 mL of 1×TAE buffer to obtain a 1% agarose matrix. The agarose gel was stained by adding 10 µL of 10,000× GelRed (Biotium) to visualize DNA under UV light at a wavelength of 302 nm. The agarose gel was placed in the electrophoresis chamber (BioRad) followed by adding 1×TAE buffer until the gel was completely submerged. DNA samples were prepared by mixing 15 µL of DNA with 1.5 µL of 5× Nucleic Acid Sample Loading Buffer (BioRad). Each DNA sample was placed in its appropriate well, and run at 100 V (constant) for 40 minutes.

Results and Discussion

The real-time biosensing of telomerase activity at an IDA microchip can be divided into three main parts: Temperature control, biosensor microchip and electrochemical measurements. FIG. 2b shows the mechanism responsible for the expected change in the impedance during incubation at 37° C. First, (1) the SAM of the TS probe specific for telomerase binding was formed at the interdigital electrodes surface, and it is in contact to the telomerase-positive nuclear extract solution exactly at the moment of its addition. Then, (2) while the biosensor IDA microchip is incubating at 37° C., the telomerase enzyme binds to the TS probes tethered to the gold surfaces due to its specificity and starts the TS elongation. These probes act as a specific substrate for telomerase due to the oligomer sequence 5'-TTAGGG-3' recognized by its RNA component as a template used in the reverse transcriptase reaction. After that, also during incubation, additional (3) telomerase enzymes start binding to their substrate, TS, at the IDA surfaces and start the elongation, adding to the previously bound enzymes. The binding and growth exerted by the telomerase enzymes produce a blocking layer that hinders electrochemical surface reactions at the IDA, which we used as the signal change in our unlabeled biosensor microchip. Finally, (4) the telomerase enzymes continue elongating of the probes. The blocking layer reaches a thickness where the kinetics of the electrochemical surface reactions is too slow. Any further change is too small to be measurable and the change in electron transfer reaches an asymptote.

Temperature Control

The present invention provides an interdigital microelectrode Au array biosensor operated by a circuit and software which controls and records the temperature vs. time in-situ. The software was connected to the temperature controller through a TTL-232R-3V3 USB-to-UART cable (FTDI) to a PIC24FJ32GP002 (Microchip) which handled all the signal processing. Using a high input impedance operational amplifier TLC2264 (Texas Instruments) as a buffer, and a 24-bit digital-to-analog converter (DAC) ADS1210 (Texas Instruments), we built an inexpensive high speed/high resolution temperature controller. Depending on the biosensor design, a lower resolution DAC may also be used, which can decrease the final cost of the device. In addition, the change of the ADS1210 to an ADS1211, or any of many others possibilities, provide a way to extend the device to control additional biosensors with the same controller. In addition, a high-quality, low-noise voltage reference for the resistance temperature detector (RTD) was achieved using a high precision resistance (Vishay Foil Resistors) with 0.01% tolerance, together with a REF02BP (Texas Instruments)+5 V precision voltage reference. Finally, an optocoupler was used to isolate the electronic circuit from the solid-state switch 2SK2617LS (Sanyo) that controlled the heater.

One important characteristic for the ssDNA probe elongation by the enzyme telomerase is the in-situ incubation. Telomeres are elongated in the human body by this enzyme at ca. 37° C. which is the temperature selected for our biosensor microchip used in this study. Telomerase biosensors previously reported in the literature need to be incubated inside an incubator or thermal cycler, depending on the experimental conditions assayed. Regardless, promoting the lengthening of a probe on a surface or the Telomeric Repeat Amplification Protocol (TRAP) assay, this later step was unavoidable before measurement and, in turn, for telomerase activity detection. Hence, the experiment needed to be stopped until the incubation period was finished, and tested either electrochemically, optically, etc. Thus, resulting not only in the need of heavy equipment but also in the impossibility of real-time measurements while the oligonucleotide elongation is happening. Moreover, although procedures such as real time PCR may be used, they also need sophisticated and expensive equipment, labels and extensive purification procedures due to its reliance on fluorescence for measurement. The present invention avoids these complications and maintains the temperature control, measurements, and electrochemical detection in real-time of the telomerase activity.

IDA Electrode and Supporting System

Figure 1:
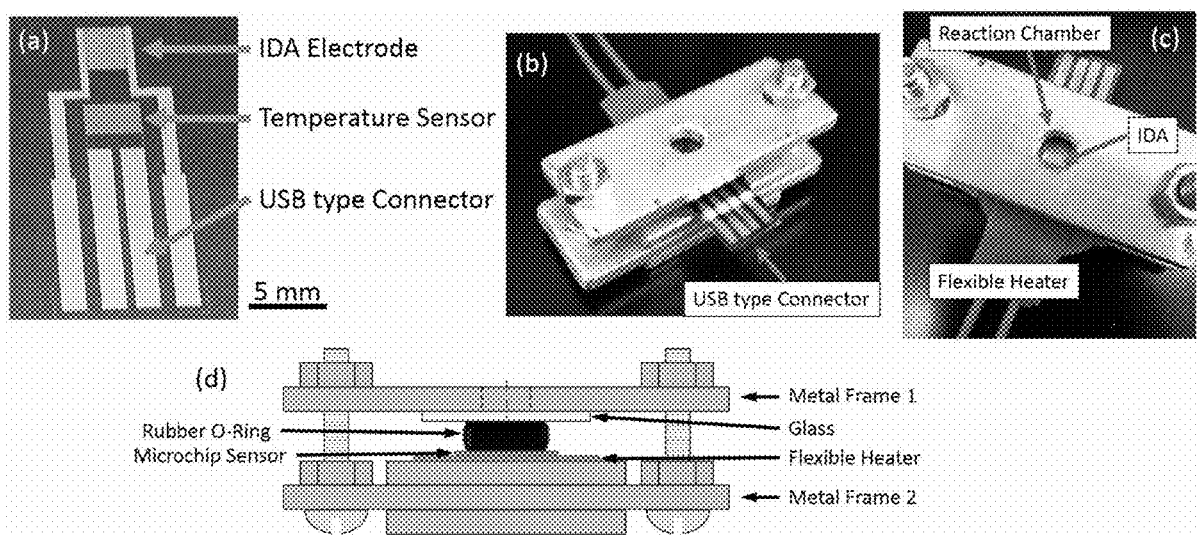
FIG. 1 show images of (a) the biosensor microchip made by photolithography, (b) and (c) the system used for heating the connecting the biosensor, and (d) a scheme of our device closed and ready for measurements.

We designed a biosensor microchip with an integrated RTD, which consists of a 10 µm path in a serpentine-shaped pattern that is accessed through the internal contacts of the USB-type connector. In addition, the biosensor microchip consisted of two 100-finger interdigital array (IDA) electrodes connected to the external contacts. These elements were connected using a standard type-A female USB cable, and a finished biosensor microchip is shown in FIG. 1a, with a total size of 1 cm×2 cm×500 µm. The resistance measured at the two middle gold connectors is previously calibrated and correlates with the temperature of the IDA biosensor. The RTD was designed to be on the same substrate next to the sensor array for accurate temperature control.

The accuracy in temperature measurement during detection in real time is very important. Thermocouples, thermistors and other commercially available temperature sensors are covered with a packaging that delays accurate temperature measurements resulting in false values, and have different thermal properties, which may result in different steady-state temperatures. Moreover, the delay due to the volumetric heat capacity would prevent rapid changes in temperature required for accurate control.

Each of the two electrodes of the interdigitated microarray connected to the external pins is used for impedance measurement. The impedance was measured in a two electrode configuration, with the working electrode connected on the left electrode and the counter and reference electrodes together connected on the other one.

A support system was built for the microchip shown in FIGS. 1b, 1c, and 1d. FIGS. 1b and 1c show the two aluminum sheets placed firmly together with screws and nuts, with a 1" dia. silicone flexible heater used for rapid changes in temperature (All Flex, Inc.) in contact with the biosensor microchip, which provides a fast temperature response. The reaction chamber was built using a rubber O-ring that enclosed the microelectrode sensor array with a glass slide on top. The volumetric capacity depends on the size of the O-ring, commonly being close to 20 µl. Even though 37° C. does not promote fast evaporation, since we used a few microliters, we found out that the reaction chamber was needed to avoid solution evaporation during the experiments and further change in concentration. A clear scheme of the setup is shown in FIG. 1d.

Figure 3:
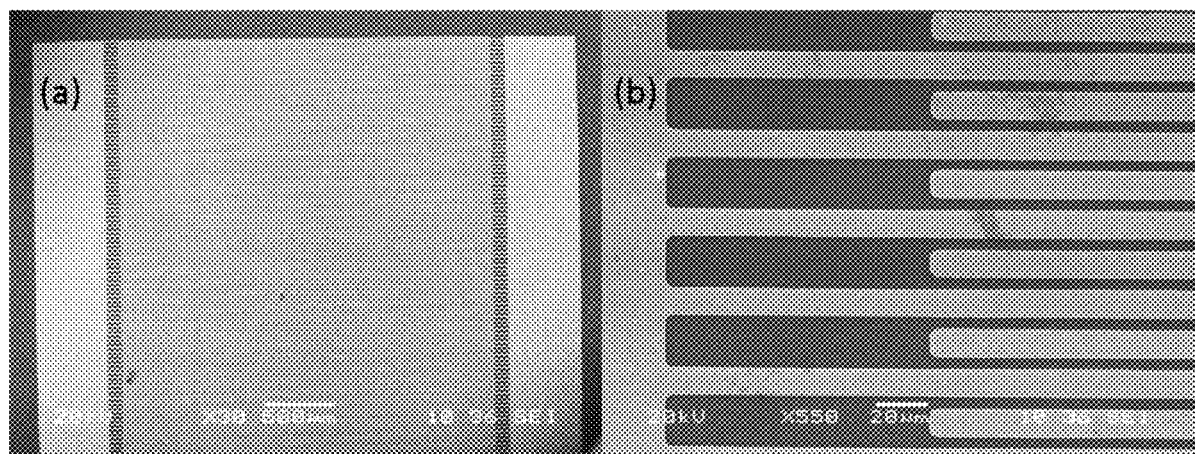
FIG. 3 shows scanning electron microscopy images of the interdigital gold electrode array.

The design of the IDA microchip electrode maximizes the interaction between the electrodes. An IDA was designed with a finger width of 10 µm and a separation of 5 µm between the fingers. After construction, the finger width was ca. 10.5 µm and the separation between the fingers ca. 4.5 µm. A scanning electron microscope (SEM) image of the IDA is shown in and a close-up in FIG. 3b. The theoretical area of each electrode was designed to be ca. 4.5 mm, and the perimeter of closest contact at 52 cm.

Electrochemical Experiments

We designed an unlabeled biosensor microarray avoiding the addition of labeling redox coupled molecules to provide electron transfer reactions such as ferrocyanide/ferricyanide. Instead, we took advantage of the nuclear cell and buffer to prepare a system that would allow for a rapid unlabeled detection of telomerase-positive nuclear extract of cancer cells, small, and robust.

First, the IDA was treated with piranha solution to clean all organic materials left from the photolithography process. Then, we used CV at 100 mV/s, from 0.3 V to 1.5 V vs Ag|AgCl in 0.5 M $H_2SO_4$ to verify that the gold surface was cleaned and both electrodes were homogenous in surface area. The TS probe was tethered to the gold surface as explained above, and the electrodes were used the same day that were modified. The sensors were maintained at 37° C. with our temperature controller and a measurement was taken every 5 minutes with the potentiostat. The open circuit potentials between the two electrodes before starting the experiments were less than or equal to 0.02 V. The impedance measurements were done from 1 MHz to 0.1 Hz, with a voltage amplitude of 10 mV at a fixed voltage of 0.00 V between the two electrodes. Between measurements, the electrodes were left at open circuit to avoid any electron transfer.

Figure 4:
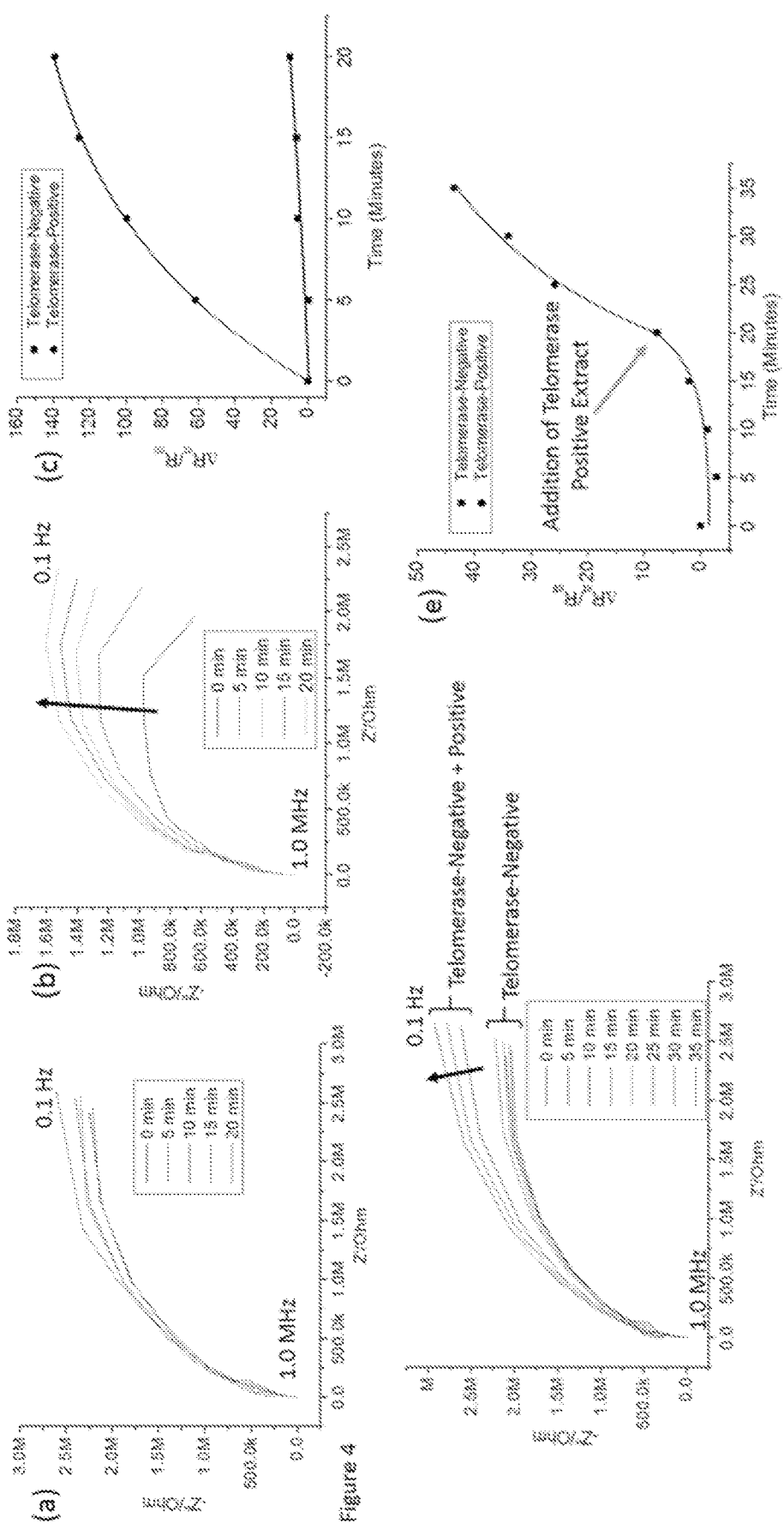
FIG. 4 shows Nyquist plots of the Electrochemical Impedance Spectroscopy results.

Nyquist plots were used to compare the EIS measurements of the biosensor IDA microchip with the telomerase-positive and telomerase-negative extracts as seen in FIGS. 4a and 4b, respectively. Both electrodes showed Voigt circuits with at least three reactions that can be noted in the Bode plots by the Phase peaks (not shown). This may be due to at least three different reactions, or more than one reaction occurring at both electrodes with different chemical kinetics. These reactions are provided by the vast compounds between the Buffer C used for the nuclear extract, and the nuclear extract itself, without the need of an external labeling agent. These results are consistent with a two-electrode system where both electrodes are similar (although never equal) and differ, even slightly, from each other in their surface properties. In these Nyquist plots, even though only one reaction can be appreciated, the one with the lowest kinetics that is observed at the lowest frequencies scanned is the most affected by telomerase binding and elongation.

It is clear from these plots that both electrodes experience significant changes in impedance in less than 20 minutes. However, the changes are quantitatively different. FIG. 4c shows the charge transfer resistance (Rct) calculated with the FRA Software (Autolab) for this analyzed reaction vs. time results. Modeled with an asymptotic exponential equation seen as a black line, the change in Rct is significant in only 20 minutes. The telomerase-negative sample showed also a change in time; however, these changes may be attributed to different reasons. The changes experienced by the control electrode may be attributed to chemical changes in the solution and surface that occurred at 37° C. as well as temperature stabilization, that are also happening at the telomerase-positive electrodes. For example, even though the O-ring provides a very good seal we may not avoid evaporation completely, which in turn changes the electrolyte concentration with time. Not only evaporation, but also, non-specific adsorptions can impact greatly the change in impedance. Since both electrodes suffer the same changes, we can attribute the difference in Rct vs. time to the elongation of the TS primer tethered to the IDA electrode surface.

These two electrodes differ in their absolute values due to variability in the construction and modification process, and to verify these results we repeated these experiments using the same electrode by doing an additive experiment. We tested 10 µl of the heated control solution in our biosensor IDA microchip, and after 20 minutes, we added 10 µl of $10^5$ cells/ml Jurkat nuclear extract solution. FIGS. 4d and 4e show the Nyquist plot and the percent change in Rct with time, respectively. Again, the results follow a Voigt circuit with phase peaks similar to the electrodes explained before, and the diameter of the half circle increases with time, due to the elongation of the surface tethered primer TS. The percent change in Rct stays below 10% until 20 minutes where the telomerase-positive solution was added, and it raises up to ca. 45% in 15 minutes.

The tethering and elongation of the TS probe due to telomerase binding and reverse transcription with the reversibility of the electron transfer process at the Au surface was studied by cyclic voltammetry (CV). The CV was conducted in a 3 electrode system with both electrodes of the biosensor microchip used as the working electrode, a Pt wire as counter and Ag|AgCl as reference electrodes. A solution of 0.1 M PBS with 0.1 M KCl at pH 7.0, 1 mM of $K_3Fe(CN)_6$ and 1 mM $K_4Fe(CN)_6$ was used for the CV studies. FIGS. 5a-c show the CV for Au, Au/TS, and Au/TS-elongated for 20 minutes at 37° C. with the telomerase-positive solution of $10^5$ cells/ml, respectively, from 10 to 300 mV/s in scan rates. FIG. 5d shows the CV for Au/TS-elongated after 4 months at room temperature in contact with telomerase-positive solution in a humidity-saturated enclosure to avoid evaporation. FIG. 5e shows the CV for Au/TS-elongated (Long Time) for 4 months and stripped using 20 µl of 0.1 M PBS solution and chronoamperometry for 2 min at 1.3 V. This voltage was applied using one of the two IDA electrodes as working electrode, and connecting the second IDA electrode to the reference and counter electrode cables together. Before the experiments, all these electrodes were washed thoroughly with nanopure water and 0.1 M PBS solution. These CV differentiate clearly in the shape of the oxidation and reduction peaks while after 4 months at room temperature the peaks are not even seen for several scan rates. From these CV, the separation of the oxidation and reduction peaks ($\Delta E_{p-p}$), and the oxidation and reduction peak currents, $i_{ox}$ and $i_{red}$, respectively, were plotted versus the square root of the scan rates ($v^{1/2}$) in FIGS. 5f-h.

First, $\Delta E_{p-p}$ decreases after the formation of the SAM compared to the clean gold electrode that is attributed to a more reversible electron transfer process due to faster kinetics. It is known that ssDNA has isoelectric point of 4.0-4.5 with a negative charge when exposed to a pH 7.0 solution, and Ferricyanide and Ferrocyanide have negative charge which may suggest a slower electron transfer. However, we observed faster kinetics and enhanced reversibility as previously seen by L. Qingwen et al. when using a SAM of L-cysteine at Au and I. Feliciano-Ramos et al. when having a SAM of L-cysteine at Pd electrodes, both incorporated herein by reference. Both groups worked at pH 7.0 and, although the carboxyl group has a negative charge, they attribute the enhanced reversibility to the local positive charge density of the amine. Therefore, even though TS has a net negative charge density, the localized positive charge densities of the amine groups may help the electron transfer process when the ssDNA is short enough, improving the reversibility as seen in our results. However, the reversibility of the electron transfer process in TS post-elongation, as shown in FIG. 5f, was affected by the increase of the $\Delta E_{p-p}$ after 20 minutes in contact with the telomerase-positive solution. Compared to TS pre-elongation, the increment from 59 mV at 10 mV/s, and 85 mV at 300 mV/s, to 70 mV and 94 mV, respectively, is due to the two mechanisms responsible for the biosensing, the telomerase binding to the TS probe and the elongation of the TS probe at the electrode surface. The $i_{ox}$ and $i_{red}$ peak currents were also affected not only decreasing but also deviating from the linearity versus $v^{1/2}$ as it is seen in the TS pre-elongation biosensor. This deviation from linearity at higher scan rates can be associated to a slower electron transfer process due to the blocking effect provided by the telomerase binding to the TS probe and its elongation.

Figure 5:
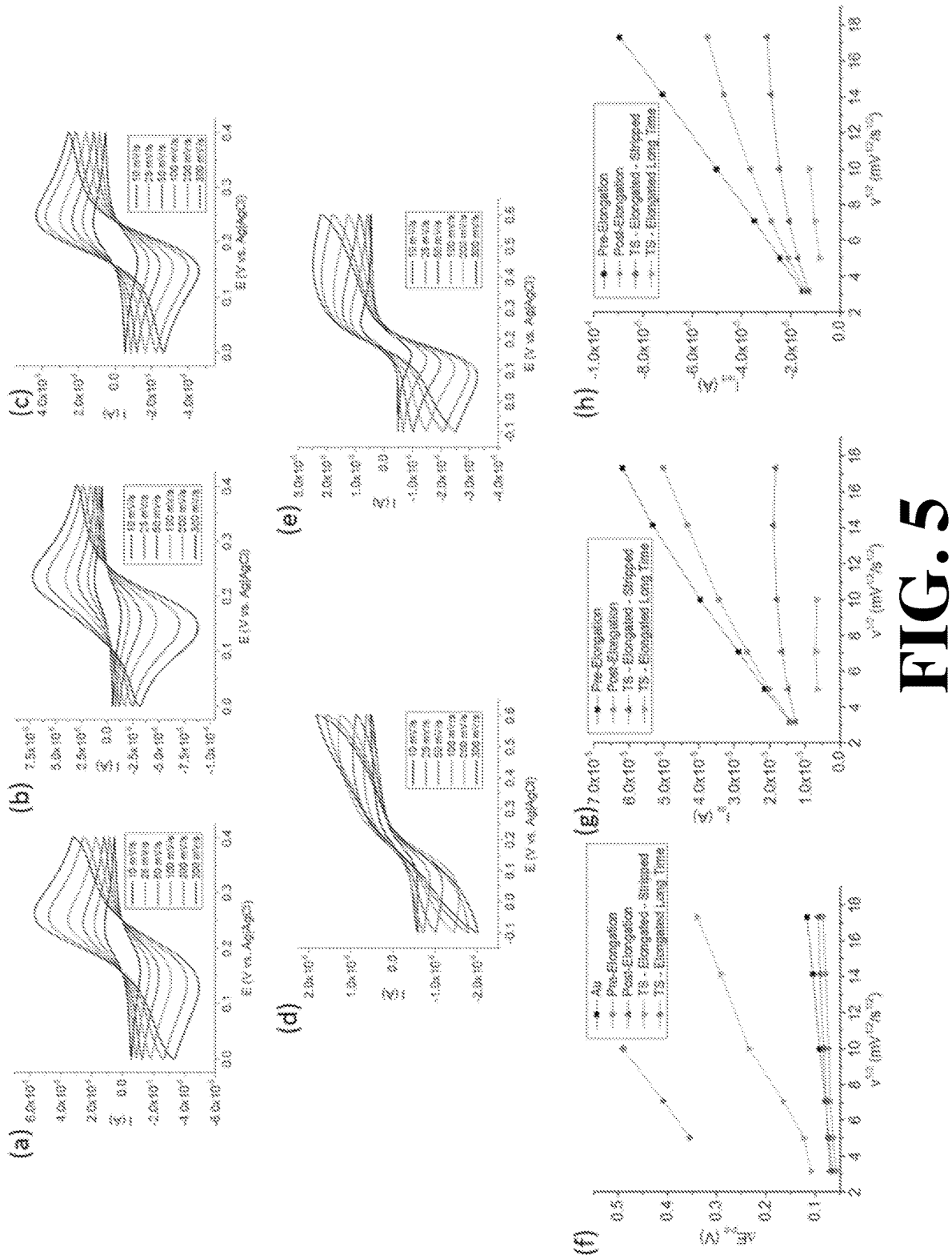
FIG. 5 shows electron transfer analysis for (a) Au, (b) Au-TS pre-elongation, (c) Au-TS post-elongation, (d) after 4 months, (e) after 2 mins at 1.3 V for non-specific binding desorption and of each electrode using (f) $\Delta E_{p-p}$, (g) $i_{ox}$ and (h) $i_{red}$ versus $v^{1/2}$.
Figure 6:
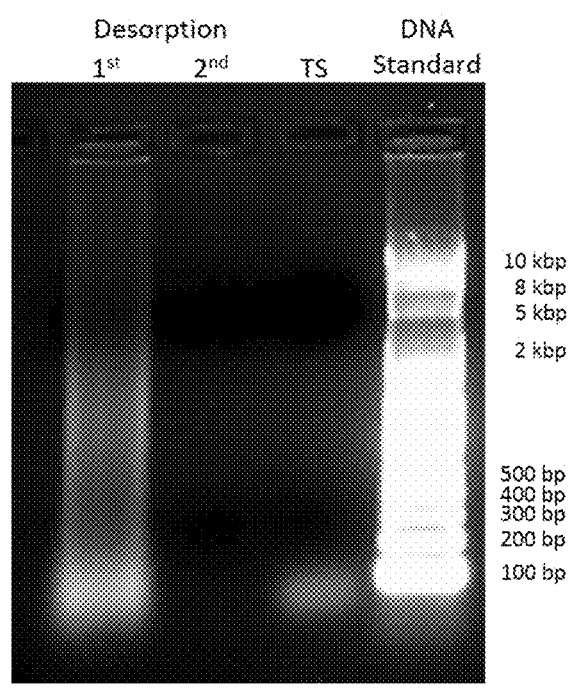
FIG. 6 shows agarose gel electrophoresis of the $1^{st}$ and $2^{nd}$ potentiostatic desorption, together with TS and a 10 kbp DNA ladder, stained using GelRed.

After 4 months at room temperature, $\Delta E_{p-p}$ increased dramatically not only due to the elongation but also probably due to non-specific surface interactions produced by the degradation products of the nuclear extract components. In order to avoid these interactions, a voltage of 1.3 V between the two electrodes was applied during 2 min, and after that, the connectors were swapped and the electrode used as working electrode was used as reference/counter electrode and viceversa, and 1.3 V was applied for 2 min. The 20 µl PBS solution from the first and the second chronoamperometry, and a solution of the TS probe were used in an Agarose gel electrophoresis (AGE) separation study. The results are shown in FIG. 6 next to the 10 kbp DNA ladder. In the first column we observed degradation fragments which were adsorbed to the electrode surface before the stripping procedures. In the second column, the absence of a line confirms that at least most of the adsorbed species were stripped from the electrode. In the third column, we observed one line at the bottom corresponding to the TS probe. The biosensor microchip after the stripping process should have a surface covered mostly by the elongated TS probe, as nothing else was observed in the second column of the AGE. After the chronoamperometry, the electron transfer process was faster with better reversibility as depicted in FIG. 5$f$ (pink), shown by a decrease on the $\Delta E_{p-p}$ an increase in $i_{ox}$ and $i_{red}$, and a $i_{ox}/i_{red}$ peak current ratio closer to 1, as shown in FIGS. 5$g$ and $h$ (blue).

CONCLUSIONS

The present invention provides a small and robust biosensor microchip based on two interdigital electrodes and an RTD which were connected through a female USB type-A connector. The RTD was connected to an easy and affordable software and hardware system designed to control the temperature for real-time impedimetric biosensing while incubating the samples. Taking advantage of the telomerase-positive nuclear extract (Jurkat cells) and nuclear lysis buffer, we showed the detection of telomerase activity without the addition of redox, fluorescent labels or other reagents. In under 20 minutes, we obtained up to 14-fold increase in signal when testing a telomerase-positive solution compared to a heat-inactivated telomerase-negative solution, using EIS. Thus, we believe that translating this biosensor microchip into a more affordable substrate, with the addition of a simple impedance measurement circuit can lead to an easy and fast cancer detection at the point-of-care.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. An electrochemical impedimetric biosensor for real-time Telomerase activity detection consisting of:
   a single sensing substrate including:
   a single interdigital array functionalized with a telomerase-specific DNA probe, wherein said interdigital array has a first electrode including a first connector pin and a second electrode including a second connector pin;
   a temperature sensor having a third connector pin and a fourth connector pin; and
   a computer interface connector including said first, second, third and fourth connector pins, wherein said interdigital array, said temperature sensor and said computer interface connector are formed on a same surface of said sensing substrate so that all four connector pins are provided adjacent to each other at a same edge of the computer interface connector;
   a reaction chamber completely enclosing said functionalized interdigital array; and
   a heating element.

2. The biosensor of claim 1, wherein said telomerase-specific DNA probe comprises a single-strand DNA of the sequence 5'-NH$_2$(CH$_2$)$_6$TTTTTTTTT-TAATCCGTCGAGCAGAGTT-3' (SEQ ID NO:1).

3. The biosensor of claim 1, wherein said first electrode comprises a plurality of fingers parallel to and interspaced from a second plurality of fingers of said second electrode.

4. The biosensor of claim 3, wherein each of said plurality of fingers has a width between 10-10.5 μm and the plurality of fingers have a separation of between 4.5-5 μm.

5. The biosensor of claim 1, wherein said heating element comprises a flexible heater in contact with said sensing substrate.

6. The biosensor of claim 1, wherein said temperature sensor is a resistance temperature detector.

7. The biosensor of claim 6, wherein said resistance temperature detector is configured in a serpentine-shaped pattern.

8. The biosensor of claim 6, wherein said third and fourth connector pins are used to measure the resistance of said resistance temperature detector.

9. The biosensor of claim 1, wherein said computer interface connector comprises a Universal Serial Bus (USB) connector.

10. The biosensor of claim 1, wherein said interdigital array, said temperature sensor, and said first, second, third and fourth connector pins are made of gold.

11. The biosensor of claim 1, wherein said first and second connector pins are used to measure an impedance of said functionalized interdigital array.

* * * * *